United States Patent [19]
Schwalge et al.

[11] Patent Number: 5,994,382
[45] Date of Patent: Nov. 30, 1999

[54] FUNGICIDAL MIXTURES

[75] Inventors: Barbara Schwalge, Heidelberg; Ruth Müller, Friedelsheim; Herbert Bayer; Hubert Sauter, both of Mannheim; Reinhold Saur, Böhl-Iggelheim; Klaus Schelberger, Gönnheim; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 08/983,253

[22] PCT Filed: Jul. 31, 1996

[86] PCT No.: PCT/EP96/03358

§ 371 Date: Jan. 20, 1998

§ 102(e) Date: Jan. 20, 1998

[87] PCT Pub. No.: WO97/06678

PCT Pub. Date: Feb. 27, 1997

[30] Foreign Application Priority Data

Aug. 17, 1995 [DE] Germany .......................... 195 30 172

[51] Int. Cl.⁶ .......................... A01N 37/18; A01N 43/50; A01N 43/54; A01N 55/00
[52] U.S. Cl. ........................... 514/383; 514/63; 514/259; 514/399; 514/619
[58] Field of Search ................... 514/383, 619, 514/63, 259, 399

[56] References Cited

U.S. PATENT DOCUMENTS

| | | | |
|---|---|---|---|
| 5,260,326 | 11/1993 | Sauter et al. | 514/383 |
| 5,399,579 | 3/1995 | Sauter | 514/383 |
| 5,476,868 | 12/1995 | Wingert et al. | 514/383 |
| 5,484,779 | 1/1996 | Sauter | 514/63 |

FOREIGN PATENT DOCUMENTS

| | | |
|---|---|---|
| 531 837 | 3/1993 | European Pat. Off. . |
| 645 091 | 3/1995 | European Pat. Off. . |
| 737 421 | 10/1996 | European Pat. Off. . |
| 43 09 272 | 9/1994 | Germany . |
| 2 279 568 | 1/1995 | United Kingdom . |
| 93/22921 | 11/1993 | WIPO . |
| 95/17818 | 7/1995 | WIPO . |
| 95/18789 | 7/1995 | WIPO . |
| 95/21154 | 8/1995 | WIPO . |

OTHER PUBLICATIONS

Pesticide manual (152, 317, 399, 421, 466, 508, 588, 603, 674, 83, 1000, 1030, 1144, 1174, 1245, 609 and 854.
Derwent 95/81855 CROPU (1994).
Derwent 95–81869 CROPU (1994).
Research Discl. Apr. 1993, No. 348.
Research Discl. Feb. 1995, No. 370.
Jun. 1992, No. 338, Emsworth, Research Discl.
Research Discl. 158, Feb. 1993.

*Primary Examiner*—Allen J. Robinson
*Attorney, Agent, or Firm*—Keil & Weinkauf

[57] ABSTRACT

Fungicidal mixture, comprising
a) an oxime ether carboxamide of the formula I

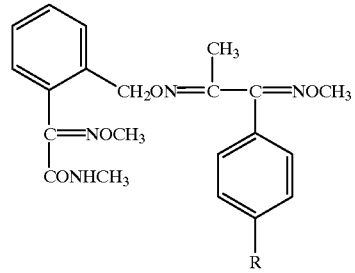

where R is hydrogen or halogen and
b) an azole derivative II selected from the group of the compounds II.1 to II.17

1-[(2RS,4RS;2RS,4SR)-4-bromo-2-(2,4-dichlorophenyl)-tetrahydrofuryl]-1H-1,2,4-triazole (II.1)

2-(4-chlorophenyl)-3-cyclopropyl-1-(1H-1,2,4-triazol-1-yl)butan-2-ol (II.2)

(±)-4-chloro-4-[4-methyl-2-(1H-1,2,4-triazol-1-ylmethyl)-1,3-dioxolan-2-yl]phenyl 4-chlorophenyl ether (II.3)

(E)-(R,S)-1-(2,4-dichlorophenyl)-4,4-dimethyl-2-(1H-1,2,4-triazol-1-yl)pent-1-en-3-ol (II.4)

(Z)-2-(1H-1,2,4-triazol-1-ylmethyl)-2-(4-fluorophenyl)-3-(2-chlorophenyl)oxirane (II.5)

4-(4-chlorophenyl)-2-phenyl-2-(1H-1,2,4-triazolylmethyl)butyronitrile (II.6)

3-(2,4-dichlorophenyl)-6-fluoro-2-(1H-1,2,4-triazol-1-yl) quinazolin-4(3H)-one (II.7)

bis(4-fluorophenyl)(methyl)(1H-1,2,4-triazol-1-ylmethyl)silane (II.8)

(R,S)-2-(2,4-dichlorophenyl)-1-(1H-1,2,4-triazol-1-yl) hexan-2-ol (II.9)

(1RS,5RS;1RS,5SR)-5-(4-chlorobenzyl)-2,2-dimenthyl-1-(1H-1,2,4-triazol-1-ylmethyl) cyclopentanol [sic] (II.10)

N-propyl-N-[2-(2,4,6-trichlorophenoxy)ethyl] imidazole-1-carboxamide (II.11)

(±)-1-[2-(2,4-dichlorophenyl)-4-propyl-1,3-dioxolan-2-ylmethyl]-1H-1,2,4-triazole (II.12)

(R,S)-1-(4-chlorophenyl)-4,4-dimethyl-3-(1H-1,2,4-triazol-1-ylmethyl)pentan-3-ol (II.13)

(±)-2-(2,4-dichlorophenyl)-3-(1H-1,2,4-triazolyl)-propyl 1,1,2,2-tetrafluoroethyl ether (II.14) and (E)-1-[1-[[4-chloro-2-(trifluoromethyl)phenyl]imino]-2-propoxyethyl]-1H-imidazole (II.15)

(RS)-2,4'-difluoro-α-(1H-1,2,4-triazol-1-ylmethyl)-benzhydryl alcohol (II.16)

2-p-chlorophenyl-2-(1H-1,2,4-triazol-1-ylmethyl)-hexanenitrile (II.17)

in a synergistically active amount.

12 Claims, No Drawings

FUNGICIDAL MIXTURES

This application is a 371 of PCT/EP96/03358, filed Jul. 31, 1996.

The present invention relates to a fungicidal mixture which comprises a) an oxime ether carboxamide of the formula I

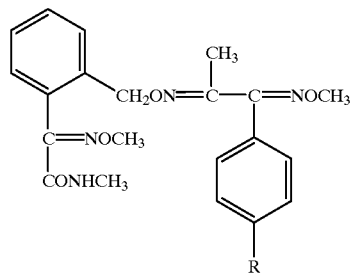

where R is hydrogen or halogen and b) an azole derivative II selected from the group of the compounds II.1 to II.17

1-[(2RS,4RS;2RS,4SR)-4-bromo-2-(2,4-dichlorophenyl)tetrahydrofuryl]-1H-1,2,4-triazole (II.1)

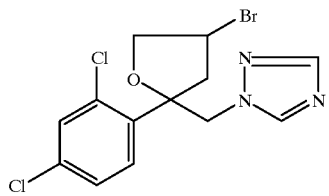

2-(4-chlorophenyl)-3-cyclopropyl-1-(1H-1,2,4-triazol-1-yl)butan-2-ol (II.2)

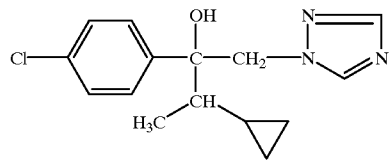

(±)-4-chloro-4-[4-methyl-2-(1H-1,2,4-triazol-1-ylmethyl)-1,3-dioxolan-2-yl]phenyl 4-chlorophenyl ether (II.3)

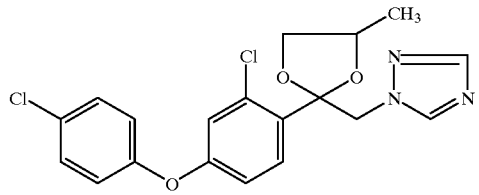

(E)-(R,S)-1-(2,4-dichlorophenyl)-4,4-dimethyl-2-(1H-1,2,4-triazol-1-yl)pent-1-en-3-ol (II.4)

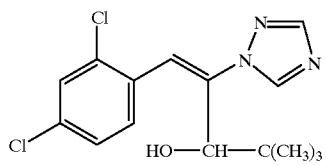

(Z)-2-(1H-1,2,4-triazol-1-ylmethyl)-2-(4-fluorophenyl)-3-(2-chlorophenyl)oxirane (II.5)

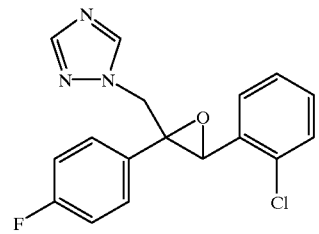

4-(4-chlorophenyl)-2-phenyl-2-(1H-1,2,4-triazolylmethyl)butyronitrile (II.6)

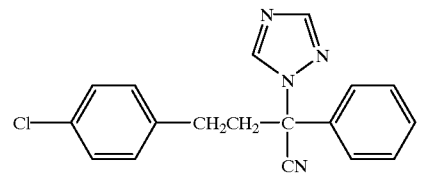

3-(2,4-dichlorophenyl)-6-fluoro-2-(1H-1,2,4-triazol-1-yl) quinazolin-4(3H)-one (II.7)

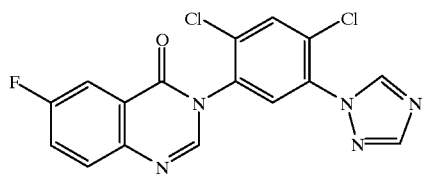

bis(4-fluorophenyl)(methyl)(1H-1,2,4-triazol-1-ylmethyl)silane (II.8)

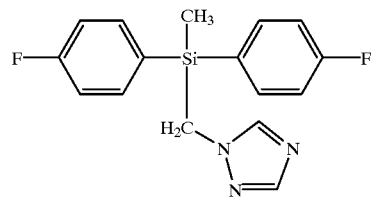

(R,S)-2-(2,4-dichlorophenyl)-1-(1H-1,2,4-triazol-1-yl) hexan-2-ol (II.9)

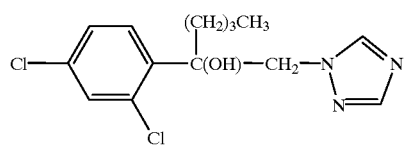

(1RS,5RS;1RS,5SR)-5-(4-chlorobenzyl)-2,2-dimethyl-1-(1H-1,2,4-triazol-1-ylmethyl)cyclopentanol (II.10)

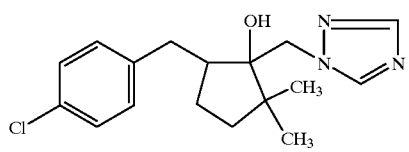

N-propyl-N-[2-(2,4,6-trichlorophenoxy)ethyl]imidazole-1-carboxamide (II.11)

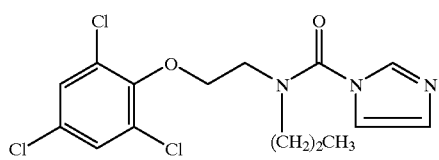

(±)-1-[2-(2,4-dichlorophenyl)-4-propyl-1,3-dioxolan-2-ylmethyl]-1H-1,2,4-triazole (II.12)

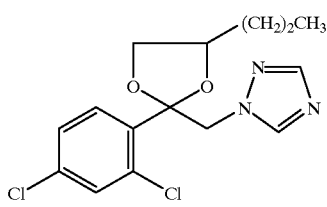

(R,S)-1-(4-chlorophenyl)-4,4-dimethyl-3-(1H-1,2,4-triazol-1-ylmethyl)pentan-3-ol (II.13)

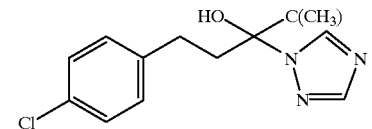

(±)-2-(2,4-dichlorophenyl)-3-(1H-1,2,4-triazolyl)propyl 1,1,2,2-tetrafluoroethyl ether (II.14) and

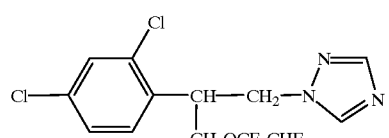

(E)-1-[1-[[4-chloro-2-(trifluoromethyl)phenyl]imino]-2-propoxyethyl]-1H-imidazole (II.15)

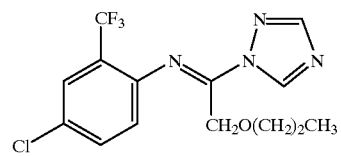

(RS)-2,4'-difluoro-α-(1H-1,2,4-triazol-1-ylmethyl)benzhydryl alcohol (II.16)

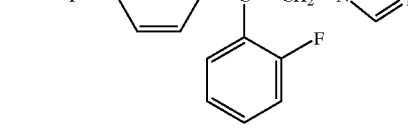

2-p-chlorophenyl-2-(1H-1,2,4-triazol-1-ylmethyl)hexanenitrile (II.17)

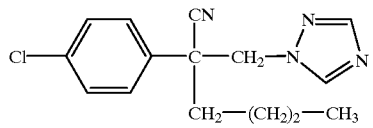

in a synergistically active amount.

Furthermore, the invention relates to methods of controlling harmful fungi using mixtures of the compounds I and II, and to the use of the compound I and of the compounds II for the preparation of such mixtures.

The compounds of the formula I, their preparation and their action against harmful fungi are known from the literature (WO-A 95/18,789). Also known are the azole derivatives II, their preparation and their action against harmful fungi:

II.1: common name: bromuconazole, Proc. Br. Crop Prot. Conf.-Pests Dis., 5-6, 439 (1990);
II.2: common name: cyproconazole, U.S. Pat. No. 4,664,696;
II.3: common name: difenoconazole, GB-A 2,098,607;
II.4: common name: diniconazole, CAS RN [83657-24-3];
II.5: common name (proposed): epoxiconazole, EP-A 196 038;
II.6: common name: fenbuconazole (proposed), EP-A 251 775;
II.7: common name: fluquinconazole, Proc. Br. Crop Prot. Conf.-Pests Dis., 5-3, 411 (1992);
II.8: common name: flusilazole, Proc. Br. Crop Prot. Conf.-Pests Dis., 1, 413 (1984);
II.9: common name: hexaconazole, CAS RN [79983-71-4];
II.10: common name: metconazole, Proc. Br. Crop Prot. Conf.-Pests Dis., 5-4, 419 (1992);
II.11: common name: prochloraz, U.S. Pat. No. 3,991,071;
II.12: common name: propiconazole, GB-A 1,522,657;
II.13: common name: tebuconazole, U.S. Pat. No. 4,723,984;
II.14: common name: tetraconazole, Proc. Br. Crop Prot. Conf.-Pests Dis., 1, 49 (1988);

II.15: common name: triflumizole, JP-A 79/119,462
II.16: common name: flutriafol, CAS RN [76674-21-0]
II.17: common name: myclobutanil, CAS RN [88671-89-0].

With the view of reducing the rates of application and improving the spectrum of action of the known compounds, it was an object of the present invention to provide mixtures which have an improved action against harmful fungi combined with a reduced total amount of active ingredients applied (synergistic mixtures).

Accordingly, we have found that this object is achieved by the mixtures defined at the outset. Moreover, we have found that, when using the compound I and the compounds II simultaneosuly together or separately or when using the compound I and the compounds II in succession, a better control of the harmful fungi can be achieved than with the individual compounds.

R in formula I is hydrogen or a halogen atom, such as fluorine, chlorine, bromine and iodine, especially hydrogen, fluorine and chlorine, in partiuclar hydrogen or fluorine.

Relative to the C=N double bond, the compounds of the formula I can be present in the E or the Z configuration (relative to the carboxylic acid function). Accordingly, they can be used, in the mixture according to the invention, either as the pure E or Z isomer or as an E/Z isomer mixture. The E/Z isomer mixture or the E isomer is preferably used, the E isomer being especially preferred.

The C=N double bonds of the oxime ether groups in the side chain of the compounds I can in each case be present as pure E or Z isomers or E/Z isomer mixtures. The compounds I can be used, in the mixtures according to the invention, as isomer mixtures, but also as pure isomers. With a view to their use, particularly preferred compounds I are those where both oxime ether groups are present in the side chain or in the E configuration (E/E).

Due to the basic character of the nitrogen atoms which the compounds I and II contain, they are capable of forming salts or adducts with inorganic or organic acids or with metal ions.

Examples of inorganic acids are hydrohalic acids, such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached to them other substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period.

The metals can be present at the various valency levels which they can assume. When providing the mixtures, it is preferred to employ the pure active ingredients I and II, with which other active ingredients against harmful fungi or other pests, such as insects, arachnids or nematodes, or else herbicidal or growth-regulating active ingredients or fertilizers, can be admixed, if desired.

The mixtures of the compounds I and II, or the simultaneous joint or separate use of the compounds I and II, are distinguished by an outstanding action against a wide spectrum of phytopathogenic fungi, in particular from the classes of the Ascomycetes and Basidiomycetes. Some of them act systemically and can therefore also be employed as foliar- and soil-acting fungicides.

They are especially important for controlling a large number of fungi in a variety of crop plants, such as cotton, vegetable species (eg. cucumbers, beans and cucurbits), barley, grass, oats, coffee, maize, fruit species, rice, rye, soya, grapevine, wheat, ornamentals, sugar cane, and a large number of seeds.

In particular, they are suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Rhynosporium Secalis, Septoria nodorum* in wheat, *Botrytis cinera* (gray mold) in strawberries and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, Alternaria species in vegetables and fruit, and Fusarium and Verticillium species.

They can furthermore be used in the protection of materials (eg. in the protection of wood), for example against Paecilomyces variotii.

The compounds I and II can be applied simultaneously together or separately or in succession, the sequence in which they are used when being applied separately generally having no effect on the result of the control measure.

The compounds I and II are usually used in a weight ratio of 10:1 to 0.1:1, preferably 10:1 to 0.2:1, in particular 5:1 to 0.2:1 (II:I).

Depending on the nature of the desired effect, the rates of application in the mixtures according to the invention are, in the case of the compounds I, 0.005 to 0.5 kg/ha, preferably 0.005 to 0.3 kg/ha, in particular 0.01 to 0.3 kg/ha. In the case of the compounds II, the rates of application are, accordingly, 0.01 to 1 kg/ha, preferably 0.05 to 1 kg/ha, in particular 0.05 to 0.5 kg/ha.

The application rates generally used for seed treatment are from 0.001 to 50 g of mixture/kg of seed, preferably 0.001 to 10 g/kg, in particular 0.01 to 5 g/kg.

If phytopathogenic harmful fungi ate to be controlled, the separate or joint application of the compounds I and II or of the mixtures of the compounds I and II is effected by spraying or dusting the seeds, the plants or the soils before or after sowing the plants or before or after plant emergence.

The fungicidal synergistic mixtures according to the invention or the compounds I and II can be applied, for example, in the form of ready-to-spray solutions, powders and suspensions, or in the form of highly concentrated aqueous, oily or other suspensions, dispersions, emulsions, oil dispersions, pastes, dusts, materials for spreading or granules, by means of spraying, atomizing, dusting, spreading or pouring. The use form depends on the intended use; in any case, it should guarantee as fine and uniform a distribution of the mixture according to the invention as possible.

The formulations are prepared in a manner known per se, eg. by adding solvents and/or carriers. Inert additives, such as emulsifiers or dispersants, are conventionally admixed with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol, polyglycol ethers or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignosulfite waste liquors or methylcellulose.

Powders, materials for spreading and dusts can be prepared by mixing or jointly grinding of the compounds I or II or of the mixture of the compounds I and II with a solid carrier.

Granules (eg. coated granules, impregnated granules or homogeneous granules) are conventionally prepared by binding the active ingredient, or active ingredients, to a solid carrier.

Suitable fillers or solid carriers are, for example, mineral earths, such as silica gel, silicic acids, silica gel, silicates, talc, kaolin, limestone, lime, chalk, bole, loess, clay, dolomite, diatomaceous earth, calcium sulfate, magnesium sulfate, magnesium oxide, ground synthetic materials, and also fertilizers, such as ammonium sulfate, ammonium phosphate, ammonium nitrate, ureas, and products of vegetable origin, such as cereal meal, tree bark meal, wood meal and nutshell meal, cellulose powder, or other solid carriers.

In general, the formulations comprise from 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR or HPLC spectrum [sic]).

The compounds I or II, or the mixtures or the formulations in question are used by treating the harmful fungi, or the plants, seeds, soils, areas, materials or spaces to be kept free from them, with a fungicidally effective amount of the mixture, or of the compounds I and II in the case of separate application. Application can be effected before or after infection by the harmful fungi.

Examples of the synergistic action of the mixtures according to the invention against harmful fungi The fungicidal action of the compounds and the mixtures was demonstrated by the following experiments:

The active ingredients were formulated separately or jointly as a 10% emulsion in a mixture of 70% by weight of cyclohexanone, 20% by weight of Nekanil® LN (Lutensol® AP6, wetting agent based on ethoxylated alkylphenols, having emulsifying and dispersing action) and 10% by weight of Emulphor® EL (Emulan® EL, emulsifier based on ethoxylated fatty alcohols) and diluted with water to give the desired concentration.

The experiments were evaluated [lacuna] determining the infected leaf areas in percent. These percentages were transformed into degrees of action. The expected degrees of action of the active ingredient mixtures were determined by Colby's formula [R.S. Colby, Weeds 15, 20–22 (1967)] and compared with the observed degrees of action.

Colby's formula:

$$E = x + y - x \cdot y / 100$$

E expected degree of action, expressed in % of the untreated control, when using the mixture of the active ingredients A and B at concentrations of a and b x degree of action, expressed in % of the untreated control, when using active ingredient A at a concentration of a y degree of action, expressed in % of the untreated control, when using active ingredient B at a concentration of b If the degree of action is 0, the infection level of the treated plants corresponds to that of the untreated control plants; if the degree of action is 100, the treated plants were free from infection.

Activity against *Erysiphe graminis* var. tritici (powdery mildew of wheat)

Leaves of wheat seedlings (3-leaf stage; cultivar "Kanzler") were inoculated in parallel with triazole-resistant and triazole-sensitive powdery mildew of wheat (*Erysiphe graminis* var. tritici) and treated with the aqueous preparation of the active ingredients when the fungal infection had reached a level of approximately 5%. After approximately 24 hours, the plants were dusted with spores of [lacuna]. The plants treated in this manner were subsequently incubated for 20 days at 18–22° C. The extent of fungal development was then determined.

The test results are compiled in the tables which follow:

Activity of the active ingredients when applied separately (triazole-resistant):

| Active ingredient | Rate of application [%] | Degree of action [%] |
|---|---|---|
| I.1 (R = H) | 0.05 | 2 |
| I.2 (R = F) | 0.05 | 7 |
| II.5 | 0.05 | 2 |
| untreated control | —/— | 0 |

Activity of the synergistic mixtures according to the invention (triazole-resistant)

| Synergistic mixture | | | Degree of |
|---|---|---|---|
| Active ingredients | [%] | Ratio | action observed |
| I.1 + II.5 | 0.03 + 0.01 | 3/1 | 15 |
| I.2 + II.5 | 0.03 + 0.01 | 3/1 | 21 |

Activity of the active ingredients when applied separately (triazole-sensitive)

| Active ingredient | Rate of application [%] | Degree of action [%] |
|---|---|---|
| I.1 (R = H) | 0.05 | 1 |
| I.2 (R = F) | 0.05 | 4 |
| II.5 | 0.05 | 1 |
| untreated control | —/— | 0 |

Activity of the synergistic mixtures according to the invention (triazole-sensitive)

| Synergistic mixture | | | Degree of action | |
|---|---|---|---|---|
| Active ingredients | [%] | Ratio | observed | calculated |
| I.1 + II.5 | 0.03 + 0.01 | 3/1 | 15 | 1.99 |
| I.2 + II.5 | 0.03 + 0.01 | 3/1 | 21 | 4.96 |

We claim:
1. A fungicidal composition comprising
   a) an oxime ether carboxamide compound of the formula I

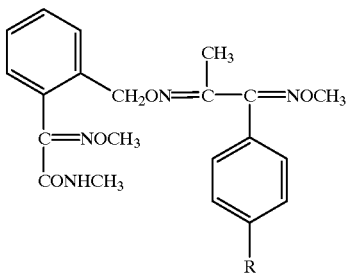

(I)

where R is hydrogen or halogen, and
   b) an azole compound II selected from the group of the compounds II.1 to II.17
   1-[(2RS,4RS;2RS,4SR)-4-bromo-2-(2,4-dichlorophenyl)-tetrahydrofuryl)-1H-1,2,4-triazole (II.1)
   2-(4-chlorophenyl)-3-cyclopropyl-1-(1H-1,2,4-triazol-1-yl)butan-2-ol (II.2)
   (±)-4-chloro-4-[4-methyl-2-(1H-1,2,4-triazol-1-ylmethyl)-1,3-dioxolan-2-yl]phenyl 4-chlorophenyl ether (II.3)
   (E)-(R,S)-1-(2,4-dichlorophenyl)-4,4-dimethyl-2-(1H-1,2,4-triazol-1-yl)pent-1-en-3-ol (II.4)
   (Z)-2-(1H-1,2,4-triazol-1-ylmethyl)-2-(4-fluorophenyl)-3-(2-chlorophenyl)oxirane (II.5)
   4-(4-chlorophenyl)-2-phenyl-2-(1H-1,2,4-triazolylmethyl)butyronitrile (II.6)
   3-(2,4-dichlorophenyl)-6-fluoro-2-(1H-1,2,4-triazol-1-yl)quinazolin-4(3H)-one (II.7)
   bis(4-fluorophenyl)(methyl)(1H-1,2,4-triazol-1-ylmethyl)silane (II.8)
   (R,S)-2-(2,4-dichlorophenyl)-1-(1H-1,2,4-triazol-1-yl)hexan-2-ol (II.9)
   (1RS,5RS;1RS,5SR)-5-(4-chlorobenzyl)-2,2-dimethyl-1-(1H-1,2,4-triazol-1-ylmethyl)cyclopentanol [[sic]] (II.10)
   N-propyl-N-[2-(2,4,6-trichlorophenoxy)ethyl]-imidazole-1-carboxamide (II.11)
   (+)-1-[2-(2,4-dichlorophenyl)-4-propyl-1,3-dioxolan-2-ylmethyl]-1H-1,2,4-triazole (II.12)
   (R,S)-1-(4-chlorophenyl)-4,4-dimethyl-3-(1H-1,2,4-triazol-1-ylmethyl)pentan-3-ol (II.13)
   (±)-2-(2,4-dichlorophenyl)-3-(1H-1,2,4-triazolyl)propyl 1,1,2,2-tetrafluoroethyl ether (II.14)
   (E)-1-[1-[[4-chloro-2-(trifluoromethyl)phenyl]imino]-2-propoxyethyl]-1H-imidazole (II.15)
   (RS)-2,4'-difluoro-α-(1H-1,2,4-triazol-1-ylmethyl)benzhydryl alcohol (II.16) and
   2-p-chlorophenyl-2-(1H-1,2,4-triazol-1-ylmethyl)hexanenitrile (II.17)
in a synergistically active amount.

2. The fungicidal composition defined in claim 1 comprising the azole compound II.5.

3. The fungicidal composition defined in claim 1, wherein the weight ratio of the compound of the formula I to the compound II is from 10:1 to 0.1:1.

4. The fungicidal composition defined in claim 3, wherein the azole compound II is selected from the group consisting of II.1, II.4, II.5 and II.10.

5. A method of controlling harmful fungi, which comprises treating the harmful fungi, their environment, or the plants, seeds, soils, areas, materials or spaces to be kept free from said fungi with a synergistically effective amount of the compound of the formula I as defined in claim 1 and one of the azole compounds II as defined in claim 1.

6. The method defined in claim 5, wherein the compound of the formula I and the compound II are applied simultaneously together or separately, or in succession.

7. The method defined in claim 5, wherein from 0.005 to 0.5 kg/ha of the compound of the formula I are applied.

8. The method defined in claim 5, wherein from 0.01 to 0.5 kg/ha of the compound II are applied.

9. The method defined in claim 5, wherein the azole compound II is selected from the group consisting of II.1, II.4, II.5 and II.10.

10. The method defined in claim 5, wherein the azole compound II is (Z)-2-(1H-1,2,4-triazol-1-ylmethyl)-2-(4-fluorophenyl)-3-(2-chlorophenyl)oxirane.

11. The method defined in claim 8, wherein the azole compound II is selected from the group consisting of II.1, II.4, II.5 and II.10.

12. The method defined in claim 8, wherein the azole compound II is (Z)-2-(1H-1,2,4-triazol-1-ylmethyl)-2-(4-fluorophenyl)-3-(2-chlorophenyl)oxirane.

* * * * *

UNITED STATES PATENT AND TRADEMARK OFFICE
CERTIFICATE OF CORRECTION

PATENT NO.: 5,994,382

DATED: November 30, 1999

INVENTOR(S): SCHWALGE et al.

It is certified that error appears in the above-identified patent and that said Letters Patent is hereby corrected as shown below:

Col. 10, claim 1, line 7, delete "[[sic]]".

Signed and Sealed this

Fifth Day of September, 2000

Attest:

Q. TODO DICKINSON

*Attesting Officer*                *Director of Patents and Trademarks*